(12) United States Patent
Reho et al.

(10) Patent No.: US 6,830,344 B2
(45) Date of Patent: Dec. 14, 2004

(54) WEARABLE PROJECTOR AND INTELLIGENT CLOTHING

(75) Inventors: Akeseli Reho, Kankaapää (FI); Jussi Impiö, Kankaanpää (FI)

(73) Assignee: Clothing Plus Oy, Kankaanpaa (FI)

( * ) Notice: Subject to any disclaimer, the term of this patent is extended or adjusted under 35 U.S.C. 154(b) by 0 days.

(21) Appl. No.: 10/343,858

(22) PCT Filed: May 11, 2001

(86) PCT No.: PCT/FI01/00455

§ 371 (c)(1),
(2), (4) Date: Apr. 28, 2003

(87) PCT Pub. No.: WO01/86398

PCT Pub. Date: Nov. 15, 2001

(65) Prior Publication Data

US 2003/0184575 A1 Oct. 2, 2003

(30) Foreign Application Priority Data

May 11, 2000 (FI) .............................................. 20001120

(51) Int. Cl.⁷ .............................................. G03B 21/14
(52) U.S. Cl. ........................................ 353/122; 353/28
(58) Field of Search ............................ 353/28, 122, 39; 359/630

(56) References Cited

U.S. PATENT DOCUMENTS

| | | | |
|---|---|---|---|
| 5,416,310 A | * | 5/1995 | Little .................... 235/462.44 |
| 5,510,806 A | | 4/1996 | Busch |
| 5,793,032 A | * | 8/1998 | Bard et al. ............. 235/472.02 |
| 5,912,653 A | * | 6/1999 | Fitch ........................... 345/87 |
| 6,057,966 A | | 5/2000 | Carroll et al. |
| 6,140,981 A | * | 10/2000 | Kuenster et al. ................ 345/8 |
| 6,312,129 B1 | * | 11/2001 | Sisodia et al. ................ 353/31 |
| 6,371,616 B1 | * | 4/2002 | Doany et al. ................. 353/39 |
| 2002/0024512 A1 | * | 2/2002 | Terasawa et al. ........... 345/204 |
| 2004/0070563 A1 | * | 4/2004 | Robinson .................... 345/156 |

FOREIGN PATENT DOCUMENTS

| | | |
|---|---|---|
| DE | 299 09 089 U1 | 1/2000 |
| EP | 0 614 104 A2 | 9/1994 |
| JP | 9-198164 | 7/1997 |
| JP | 11-136704 | 5/1999 |

* cited by examiner

*Primary Examiner*—William C. Dowling
(74) *Attorney, Agent, or Firm*—Burns, Doane, Swecker & Mathis, L.L.P.

(57) ABSTRACT

The invention relates to a wearable display means (202) of projector type and to a garment (700). The invention relates specifically to a miniature projector (202), which is worn by the user and whose application is compatible with wearable electronic data processing systems (220, 222, 224). One concept of the invention is to project the electronic information generated by wearable electronic devices (220, 222, 224) connected to the projector (202) in the user's field of vision by means of the projector (202). The projector (202) of the invention is equipped with a matrix consisting of at least one Resonance Cavity LED or a micro-mirror and with electronics (300) and optics (314) necessary for projecting. The projector (202) and the electronic devices (220, 222, 224) are integrated in the garment (700) of the invention.

21 Claims, 3 Drawing Sheets

Figure 1:
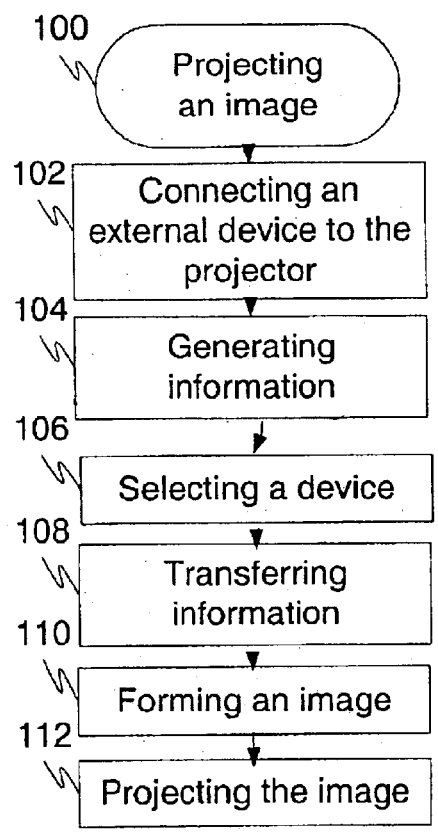

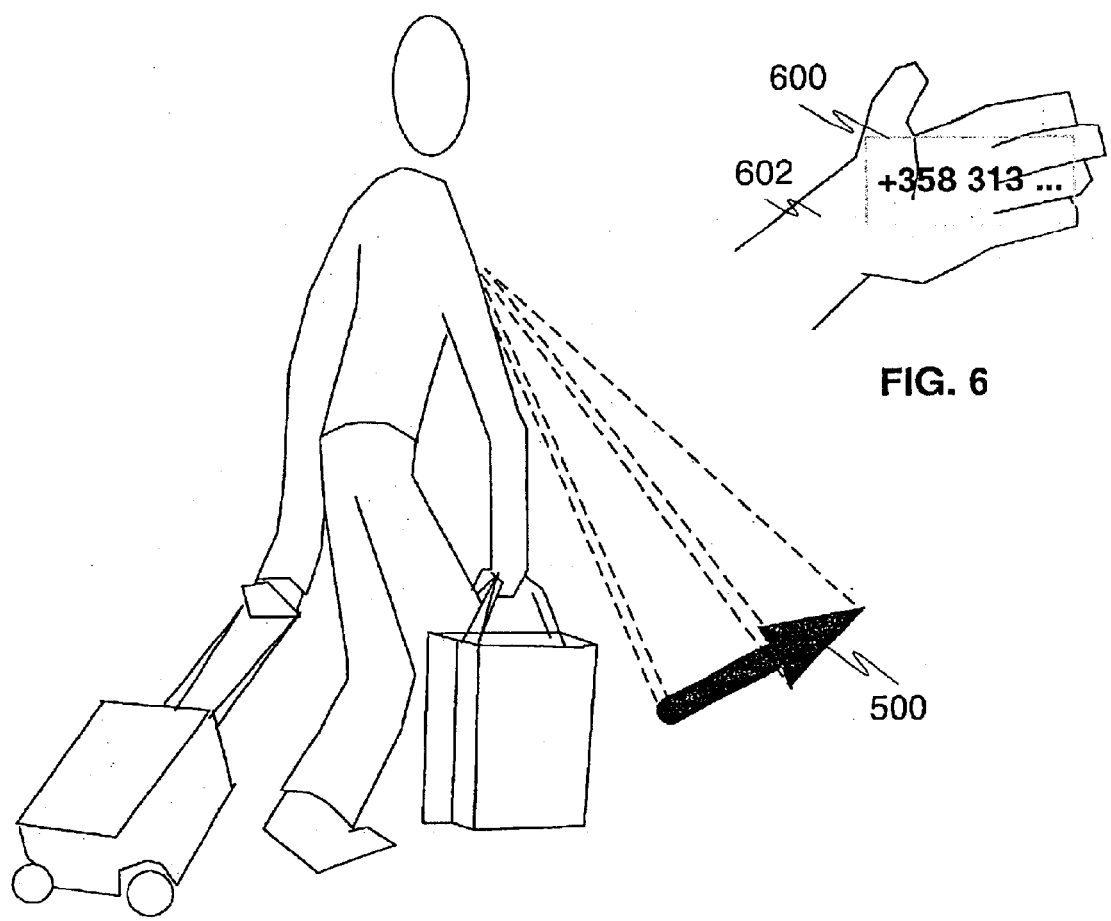
FIG. 6
FIG. 5
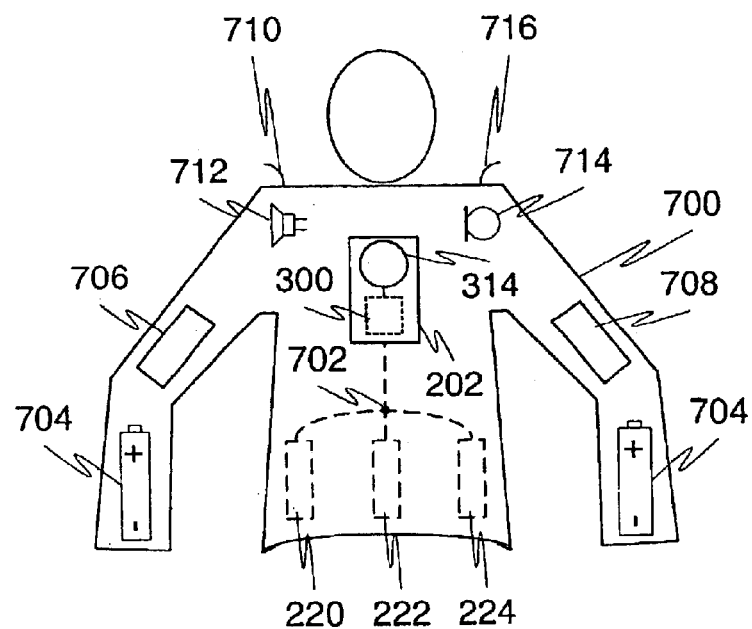
FIG. 7

WEARABLE PROJECTOR AND INTELLIGENT CLOTHING

The invention relates to a wearable display of projector type and to a garment. The invention relates specifically to a miniature projector, which the operator may wear and whose operation is compatible with wearable electronic data processing systems.

Various portable electronic devices, such as mobile stations, Personal Digital Assistants (PDA), Global Positioning System (GPS) devices and similar electronic data processing systems have been increasingly used lately, and they allow the transmission of information and services in different modes and large amounts. A user may carry simultaneously for instance a mobile phone, a PDA drive and a GPS device. All these devices usually comprise their individual display, keyboard, power source and a system intended for data transmission, such as a transceiver and an aerial.

Owing to current techniques, portable electronic data processing systems may be made in quite compact sizes, allowing the user to readily carry for instance several data processing devices. However, this involves the problem that, when the user needs to operate any of the data processing devices he is carrying, for instance a mobile station for reading a message, or a GPS device in order to check the direction or any other information, he has to bring out the device in order to read the message or any other information on the small display of the device.

The displays of portable electronic data processing devices are often liquid crystal displays, which are very difficult to read in the dark. Yet the displays are generally equipped with some kind of background light for reading in the dark. However, in this connection, there is the additional problem of the user, while using a device of the type described above, having to hold the device in his hands, so that he cannot do anything else that requires the use of his hands at the same Lime. Moreover, the user has to focus his eyes on the closely located, small and usually poorly visible display. This slows down and hampers uninterrupted movement in a demanding terrain, for instance.

Various combinations of wearable projectors and associated auxiliary equipment are known as solutions to the problem mentioned above. Thus, for instances U.S. Pat. No. 6,140,981 discloses a solution for a wearable projector, which consists of two parts: one a display means with an arm intended to be attached on the user's front side, and the other one a computer to be worn like a rucksack on the user's back. This solution comprises a liquid crystal display and control switches and buttons for controlling the computer.

U.S. Pat. No. 6,057,966 discloses a wearable miniature display, which produces an image or a screen that is reflected in the user's field of vision. The display means of this arrangement is fitted for instance in the user's spectacle rim or in any similar arrangement. The display means consists of an image source unit intended to produce an image, an apparatus intended to transmit the image, which comprises at least one optical fibre and means for bringing the image into the optical fibre, and means for passing the image from the optical fibre to a mirror. the image being reflected from the mirror to the user's eyes. The mirror is typically attached to the user's head, at his spectacle lens, with separate means resembling a spectacle rim. In one solution described in this publication. the mirror may also be a device resembling a visor, which is attached in an arrangement that the user wears on his head like a helmet. The image source unit of the display means consists of control electronics, a microphone and a loudspeaker, a liquid crystal display and optics for passing the image into an optical fibre and from there to a mirror.

However, the solutions mentioned above involve the problem of a relatively large-sized projector and not being practical in use and not having a pleasant aspect. Moreover, a user is frequently hampered in his movements by wearing the apparatus and the helmet, or the band equipped with a mirror of the solutions described in these references. A large-sized apparatus that the user wears in his garment or otherwise impedes work operations and may even cause danger in confined spaces. What is more, a mirror or helmet arrangement worn by the user may limit his field of vision. Finally, the apparatuses of the references are provided with low-powered liquid crystal displays, which are not visible in the dark. On the other hand, liquid crystal displays equipped with background light entail the problem of unreasonably high power consumption.

The purpose of the invention is to provide a solution for combining portable data processing devices and a projector that allows the user to study the information generated by the data processing device without bringing out the device itself. Another purpose of the invention is to provide a projector that is small-sized, easy to wear and self-luminous. Yet another purpose of the invention is to provide a solution that does not hamper the user's activities in use.

The purposes of the invention are achieved by combining portable electronic data processing devices with a separate wearable projector and by directing the information generated by the devices to be projected with a projector in the user's field of vision. In addition, the purposes of the invention are achieved by forming the projector display unit of a matrix that comprises at least one Resonance Cavity Light Emitting Diode (RC LED) or micro-mirror, and by providing a projector and devices that can be attached to the user's garment.

In this conjunction, an RC LED implies a component consisting of a photodiode made of semi-conductor material that operates on the quantum cavitation theory and emits very bright light when supplied with electric current. Typical features of an RC LED consist in the light beam being directed perpendicularly to the component surface and having a pure spectrum. The RC LED comprises a micro-cavity made of semi-conductor material, where electric current is transformed into light. The micro-cavity resonates with the light it has generated, so that the characteristics of emitted light are very markedly modified.

In this conjunction, a micro-mirror projector stands for a projector comprising a micro-mirror matrix, which, in turn, comprises at least one micro-mirror. Each micro-mirror in the micro-mirror matrix equals one image element, the number of which may be e.g. 500,000 within an area of the size of a button. The light from the projector lamp is typically focussed with a condensing sub-stage to the surface of the mirror matrix, from where it is reflected over an objective lens to the surface to be projected, such as for instance the user's hand, or a screen. The micro-mirror can typically assume only two positions, in one of which the light from the lamp is reflected on the screen and the mirror is seen as a bright point. In the inverse position, the light is reflected past the lens and the mirror is seen as a dark point on the screen.

In this context, a data processing device and system mean a device and a system allowing electronic data processing or a device generating information that can be displayed with the projector of the invention. In this description, data processing devices and systems imply i.a. computers.

mobile stations such as GSM, WAP and PDA devices, and also devices using GPRS services and GPS positioning devices. The data processing devices and systems described here can be specifically integrated in the user's garment.

The method of the invention for displaying electronic data generated by an electronic device with the aid of a projector is characterised by comprising steps for connecting at least one external electronic device to the projector worn by the user, generating electronic data acceptable for display with at least one of said electronic devices, selecting for projection the electronic data generated by at least one external electronic device, transferring the selected electronic data generated by the electronic device to a projector to be worn by the user, generating from the displayed electronic data an image to be projected with the projector worn by the user, projecting the image formed from the electronic data generated by the electronic device on a surface in the user's view, with the aid of a projector worn by the user.

The projector of the invention for displaying and projecting on a surface data generated by at least one electronic device is characterised by said projector being a projector that can be worn by the user, said at least one electronic device being connected to the projector and the projector comprising at least one light-emitting means for projecting the information to be displayed and also the optics and electronics necessary for projection.

The garment of the invention, which comprises at least one electronic data processing device and a connected display means for displaying information generated by the electronic data processing device, is characterised by the display means being a projector.

A number of preferred embodiments of the invention are described in the dependent claims.

The invention achieves marked benefits over prior art solutions. The method of the invention allows for an easy and straightforward method for displaying and reading information generated by portable electronic data processing apparatuses. The invention enables the user to select the device he desires to be projected in front of him. The system of the invention enables the user to read the information generated by the portable electronic data processing device while he is simultaneously performing some other task. Owing to its small space requirement. the method of the invention does not hamper the user's movements. nor does it limit the user's field of vision.

Moreover, the invention allows the user to readily control several data processing devices connected to the projector by means of one single display and control unit. Owing to the self-luminous projector, the invention allows the information generated by the devices connected to the projector to be studied even when it is completely dark. The invention also allows for long charge intervals, given the very low power consumption of the image-producing unit of the projector.

The projector of the invention can be carried out in a very small size, because the projector. optics can be separated as a physically discrete display unit from the projector electronics. Owing to its small size, the projector optics can be integrated, say, in the user's garment, requiring an area approximately of the size of a button. In addition, the projector of the invention is self-luminous and extremely bright, and is consequently easy to use also when it is dark. The method of the invention also allows the different projector components to be mutually combined and connected devices to be combined with the projector, either by wireless means or with conductors incorporated in the user's garment, so that there will be no suspended wires hampering the user's performances.

Various portable electronic data processing devices. such as for instance a mobile phone. a GPS positioning device, or a portable PDA device, can be combined with the projector of the invention. The device whose display the user wishes to project can be selected automatically for instance when the device gives a signal to this effect. This can be done for instance in a situation where the user receives an e-mail or a Shot Message Service in his mobile station. In that case, the mobile station preferably transmits a signal to the projector, which automatically projects the mobile station display in the user's field of vision, for instance on the ground in front of him. or on his hand, where he may read the message. In accordance with the invention, the user does not have to check his mobile station separately for any received e-mail or SMS, but the mail/message is automatically projected the moment it arrives.

The user may optionally select the device he wishes to display by means of a separate control unit. He may for instance press a switch on the control unit, and then the projector projects the display of the GPS positioning device in front of the user. The projected display may for instance show the user a direction arrow indicating the user's goal, together with the hour and the remaining distance and time. The projected display may be seen in front of the user also when he is moving, so that he can easily practice orienteering in the dark by simply observing occasionally the display and the arrow and any other necessary information, which are projected in front of him.

One object of use of the invention could comprise video conferences or the display of interesting information on sports performances by projecting set of meters on the pavement by means of the projector of the invention. The projector display could also show the control menus of a data processing device, which would enable the user to choose the functions he desires using an actuator.

Figure 2:
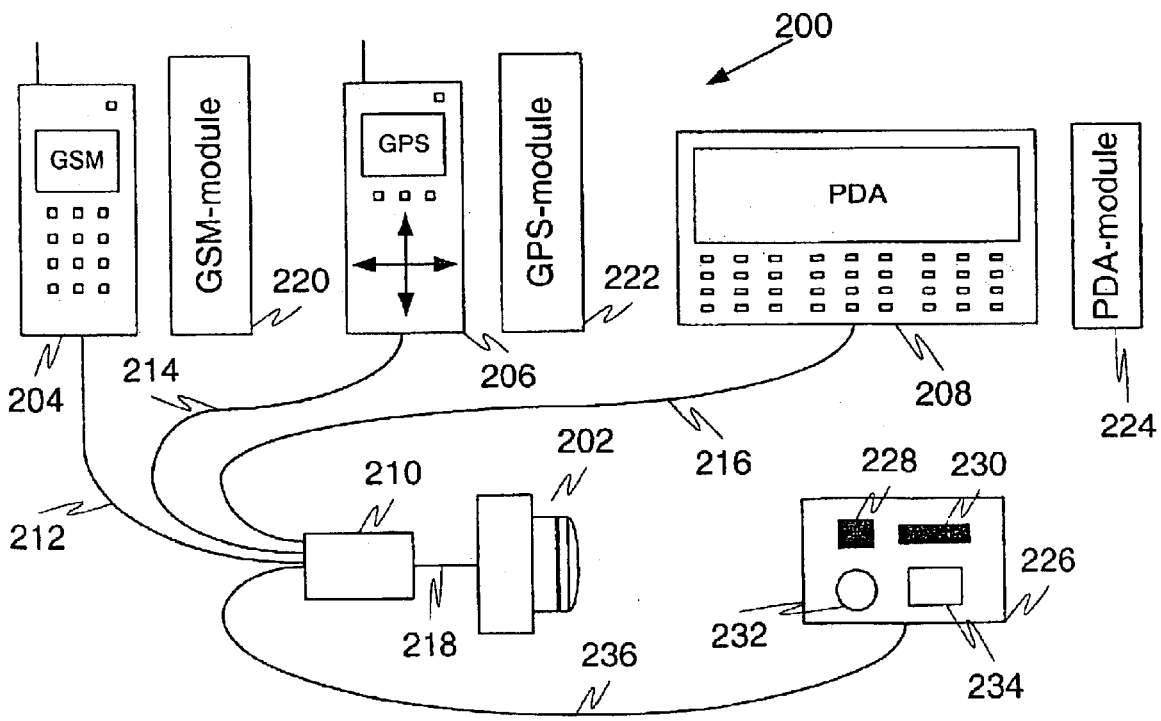
Figure 3:
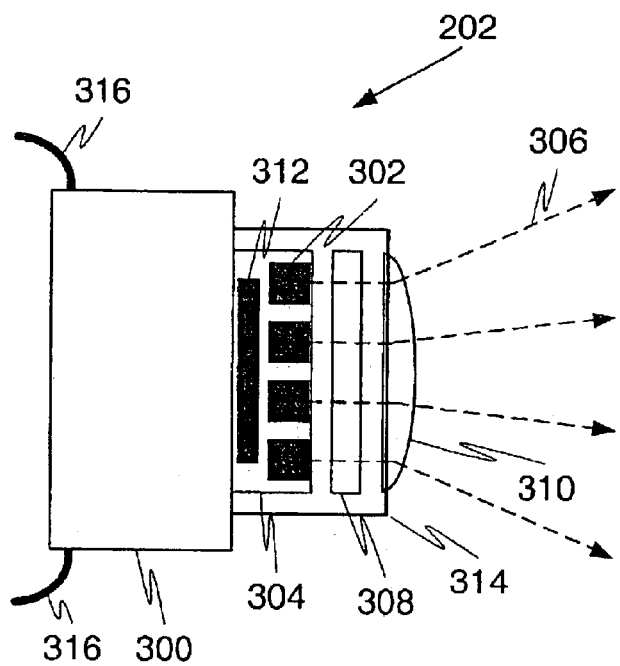
Figure 4:
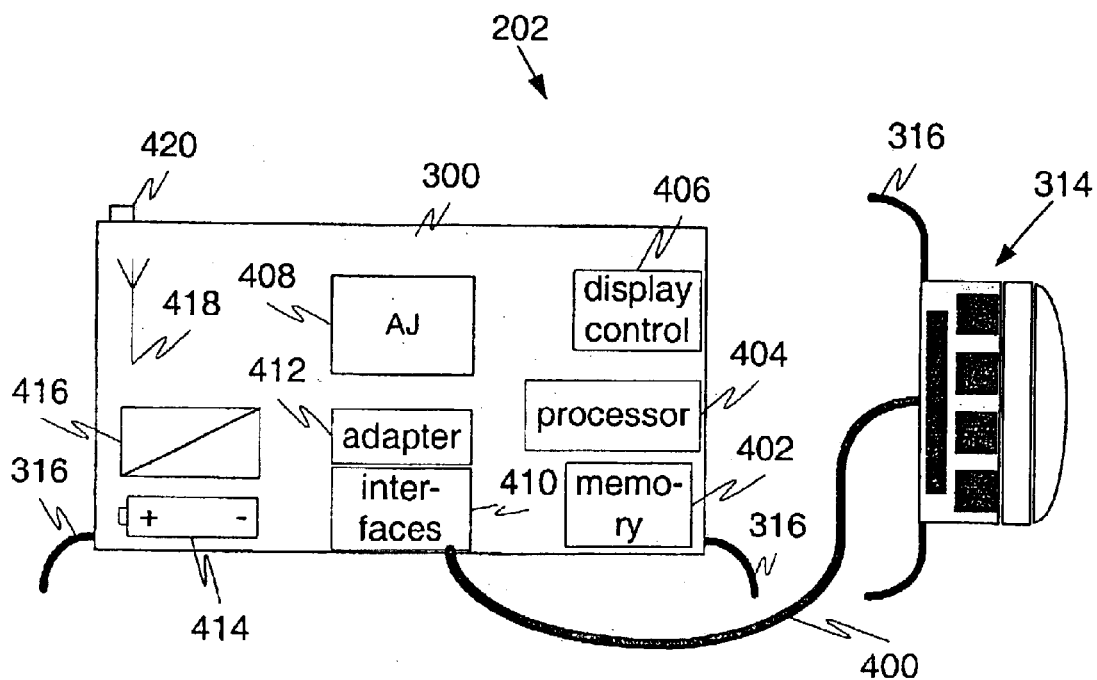

Preferred embodiments of the invention are explained in further detail in the following sections, with reference to the accompanying drawings, in which FIG. 1 shows a flow diagram of a method for projecting an image in accordance with the invention, FIG. 2 shows an arrangement of the invention for connecting portable data processing systems to the projector of the invention, FIG. 3 shows a projector in accordance with the invention, FIG. 4 shows a projector in accordance with the invention, in which the projector electronics can be detached from the projector optics, FIG. 5 shows a method of the invention for projecting an image by means of the projector of the invention, FIG. 6 shows another method of the invention for projecting an image by means of the projector of the invention, and FIG. 7 shows a garment in accordance with the invention.

FIG. 1 shows a flow diagram of a method 100 of the invention for projecting an image by means of a wearable projector equipped with a matrix consisting of RC LEDs or micro-mirrors. In step 102, at least one external electronic data processing system, such as a mobile phone, a GPS positioning device or a PDA device, is connected to the projector. The external device may be connected for instance by means of a cable or optionally by wireless means, such as for instance with Blue-Tooth techniques. The projector preferably includes a separate adapter for the connection of an external device, the projector communicating over the adapter with the external device. The adapter may also be integrated in the projector electronics.

In step 104, the external device generates information, which may consist e.g. of an SMS received by the mobile phone, a direction or position indicated by the GPS positioning device, or an electronic message or reminder from the PDA device. The information may also consist of electronic information generated by some other electronic device connected to the projector. After it has generated electronic information. such as for instance an SMS received in the mobile phone, the external device may advantageously transmit a signal to the projector, which in step 106 can select the device that emitted the signal and connect itself to project the display of this particular device in the user's field of vision. Optionally, in step 106, the user may pick the projector he desires among the connected devices, the display of this device being subsequently projected in the user's field of vision.

When the particular device has been selected whose display one wants to project. the information generated by the device is transferred to the projector in step 108, with the aid of a cable or an optical fibre or a wireless connection, for instance. In step 110, the imaging unit of the projector forms an image to be projected from the electronic information generated by the external device that it has received, and the electronic image formed in step 112 is projected in the user's field of view. The image can be projected and focussed to the desired location, as for instance a location indicated by the user. the user's hand. a table, a sheet of paper held by the user, or any other plate-like means. a wall, or on the ground in front of the user. The image may comprise any information generated by an external device, such as for instance various texts, menus, signal arrows, dates and hours.

FIG. 2 shows an arrangement 200 of the invention for connecting portable data processing systems to the projector 202 of the invention. The devices to be connected to the projector 202 may be any electronic devices, such as for instance a mobile station 204. a GPS positioning device 206 or a PDA device 208. The user may typically connect a device of the type mentioned above to the projector 202 for instance by connecting the device to the Input/Output gate of the projector 202, or to a wire 212, 214, 216 connected to a separate adapter 210, and then the projector 202 may adapt its data transmission system to this particular device. Various drivers corresponding to the devices connected to the projector may also be installed in the projector 202. In addition, the adapter 210 can be connected to the projector 202 for instance by a cable 218 or optically or over a wire-less radio connection.

Optionally, the portable data processing systems connected to the projector 202 may be modules. such as for instance a GSM module 220 a GPS module 222 or a PDA module 224. The modules may be without a display and a keyboard, or even without a power source, and then the control of the module is performed lot instance with a separate control unit 226, such as a key 228. a joystick 230, a sound control unit 232 or a mouse plate 234, and the display of the module can be projected in the user's field of vision with the projector 202 of the invention. The control unit 226 can be connected to the projector 202 or the adapter 210 for instance over a wire 236, optically or by wireless means, such as e.g. with Blue-Tooth techniques. The power supply to the module can be performed for instance over a cable, and then the garment may have a separate power source, or then the power required is also supplied from the power source of the projector. The modules can also be integrated in the user's garment in advance.

The modules can be connected to the projector 202 in the same way as the devices mentioned above by means of fibre-like cables, which may be integrated in the user's garment. The modules or the other portable electronic devices of the kind mentioned above can also be connected to the projector by optical or wireless means, such as e.g. with Blue-Tooth techniques, allowing the projector to connect to the device when the device is brought into the vicinity of the projector 202 and has been identified by the projector.

The device connected to the projector may be any electronic device, such as a pulsometer or any other sensor determining the user's body functions, such as his pulse, temperature, energy consumption, or any similar information. The device connected to the projector may also be an external device with which the user may be in data transmission communication, receiving information about his environment or himself or carry out certain actions.

FIG. 3 shows a projector 202 of the invention, which typically comprises an electronics part 300, a matrix 304 consisting of at least one RC LED or a micro-mirror 302, and optics for focussing the projecting ray 306. The optics may consist for instance of a diffractive means 308 and at least one lens 310. The projector may also comprise orientation devices 312.

The projector 202 of the invention has the typical feature of the electronic part 300 of the projector 202 being removably attachable to the optics and the matrix 304 of the projector 200, allowing the electronics part 300 to be positioned apart from the optics and the matrix. Thus the optics and the matrix can be formed as an integrated and very compact display unit, i.e. a projecting means 314. In addition, the projector 202 typically comprises means 316 for fixing the projector removably on the user, as for instance to his garment.

FIG. 4 shows the projector 202 of the invention, where the electronics part 300 of the projector has been detached from the projecting means 314 comprising the optics and the matrix of the projector 202. The projecting means 314 can be fixed discretely from the electronics part 300. e.g. to the front of the user's garment. such as a button, collar, tiepin, hat, belt, shoe or any similar suitable location. The projecting means 314 can be connected to the electronics part 300 for instance by wire-less radio connection, optically or over a cable 400. The wire-less radio connection may be e.g. a Blue-Tooth connection.

The electronics part 300 and the projecting means 314 of the projector 202 comprise fixing means 316 for fixing this part or means removably on the user, as for instance to his garment. The fixing means 316 may be e.g. means such as a belt, a press stud, an adhesive tape, a magnet or the like. The electronics part 300 and the projecting means 314 of the projector 202 may comprise separate fixing means.

The electronics part 300 of the projector typically comprises at least one memory unit 402, which comprises both a Random Access Memory (RAM) and a Read Only Memory (ROM), and also some kind of cache. The electronics part 300 may also comprise a processor 404 for data processing, a display control unit 406 for forming an image to be projected and controlling the matrix 304, and also sensing system 408, which controls the orientation device 312 of the projecting means 314. The sensing system controls the orientation device 312 to project and focus information generated by the electronics device to the location indicated by the user.

The electronics part 300 may also comprise at least one connector 410 for connecting an external device. such as an electronic data processing system or a charger. The electronics part 300 typically also comprises an adapter 412 for identifying an external device and for adapting the electronics part 300 to the external device to be connected, and a power source 414. The electronics part 300 may also comprise means, such as a radio transceiver 416, an aerial 418 and e.g. an IR transceiver 420 for connecting an external data processing system, a projecting means 314 and a control unit 226 to the electronics part 300 by wireless radio connection or optically.

FIG. 5 shows the method of the invention for projecting an image 500 with the projector of the invention on the ground in front of the user. Optionally, the image 500, which may be e.g. the display of a device connected to the projector, can also be projected on a wall. a sheet of paper or any surface of sufficient size and evenness, and of suitable colour.

The image 500 can be projected on the ground in front of the user for instance in a situation where the user is walking with his eyes at least occasionally focused on the ground immediately in front of him. The image 500 to be projected may be e.g. information on the position, direction and distance generated by the positioning device, speed data, display of the remaining time, the date or the hour. The image may also be the display of information generated by a mobile station or a PDA device, such as an SMS received by the mobile station or an electronic message. reminder or other information from the PDA device. The image may also represent information generated by a system determining the user's physiological properties, such as his pulse, blood pressure, respiratory frequency or energy consumption. The image may also be the information generated by any electronic device that can be connected to the projector.

FIG. 6 shows a method of the invention for projecting an image 600 on the user's hand 602 with the projector of the invention. Whenever the user so desires, the image 600 can be projected on the user's hand 602 for instance in situations where no suitable surface is otherwise available, or when the user does not want an SMS or similar information to be seen on the ground, where other people can read it as well.

FIG. 7 shows a garment 700 of the invention, comprising the projector 202 of the invention exploded with the projecting means 314 fixed to the front of the garment 700 and the electronics part 300 placed elsewhere in the garment 700. The garment 700 also contains various integrated electronic modules for various data processing purposes, such as e.g. a GSM module 220, a GPS module 222 and a PDA module 224. The garment 700 also comprises a fibre-like wire net 702 integrated in the garment 700, the wire net being connected to the electronics part 300 of the projector and with external electronic devices being connectable to the wire net 702.

The garment 700 may also have an integrated separate power source 704 or a solar panel 706, which may be connected to the projector 202 and the modules 220, 222, 224 over the fibre-like wire net 702 integrated in the garment 700. The garment 700 may additionally comprise means 708 for charging the power source 704, allowing the user to charge the power sources 704 in his garment by connecting the charging wire for instance to an electric plug 710 in the wire net 702 in the garment 700. Optionally. the power sources in the garment 700 can be charged also by means of a solar panel system 706 provided in the garment.

The garment 700 may also comprise at least one loudspeaker 712 and a microphone 714, allowing the user to receive an incoming call for instance in a mobile station or similar module in the garment 700. The loudspeaker 712 and the microphone are typically connected to the electronics part 300 of the projector. The garment 700 may additionally comprise an integrated means for receiving radio programmes, and then the radio programme can preferably be announced over the loudspeaker 712. The user may also speak in his mobile station over the microphone 714, and dictate messages in a device integrated in the garment 700, such as a PDA device or module.

The garment 700 may further comprise at least on aerial 716, which may project slightly from the garment 700, or optionally the aerial 716 may be integrated in the garment 700. The aerial 716 may be connected to the electronics part 300 of the projector and over the electronics part 300 to modules integrated in the garment 700, e.g. over a wire net 702 in the garment 700. The aerial 716 may preferably act as an aerial for all the devices or integrated modules in the garment 700, such as e.g. GPS or GSM modules.

The garment 700 or the electronic part 300 of the projector may also have an interface. such as an optical or wireless connection or a cable connection. by means of which the garment 700 or the projector can be connected for instance to a personal computer for data updating.

Only a number of preferred embodiments of the invention have been described above. The principle of the invention can naturally be varied within the scope of protection defined by the claims, regarding for instance details of the embodiment and the fields of use. Specifically, most varied electronic devices can be connected to the projector. The devices, control units and various projector components can be interconnected with a cable, e.g. a direct optical connection or with an optical fibre, by wireless radio connection, or by any other similar data transmission method.

Moreover, it should be noted that the projector component, the components integrated in the garment and the power sources can be positioned arbitrarily all over the user's body, and that the garment of the invention may be e.g. a shirt, a coat. a pair of trousers, a shoe. a glove or a hat. or any other similar piece of clothing. The piece of clothing may also be a small bag or belt fixed at the user's waist or elsewhere on his body.

The projector of the invention may be e.g. a laser projector, a video projector, a micro-mirror projector equipped with a micro-mirror matrix (304), the matrix (304) comprising at least one micro-mirror (302) or a projector equipped with an RC LED matrix (304), the matrix (304) comprising at least one resonance cavity LED (302).

What is claimed is:

1. A method for displaying electronic information generated with an external portable electronic device by means of a projector, where the electronic device is a mobile station, GPS positioning device, data processing device of PDA type, pulse meter, sensor determining a user's body functions, or device for showing time, the method comprising:

connecting the external portable electronic device to a separate wearable projector worn by the user;

generating electronic information acceptable for display with at least one of said electronic devices;

selecting for projection the electronic information generated by at least one external device;

transferring the selected electronic information generated by the electronic device to the projector attached to a garment worn by the user;

forming from the electronic information to be displayed an image to be projected with the projector attached to the garment worn by the user, and projecting the image formed from the electronic information generated by the electronic device on a surface in the user's field of vision by means of said projector attached to the garment worn by the user.

2. A method as defined in claim 1, wherein the selection of the electronic device, which generates information for display, is performed automatically as the electronic device generates a signal.

3. A method as defined in claim 1, wherein the user performs the selection of the external device by means of a control unit.

4. A method as defined in claim 1, wherein the electronic information generated by the electronic device is projected on the user's hand, around or sheet of paper.

5. A projector adapted to display and project on a surface electronic information generated by at least one portable electronic device, wherein at least one electronic device is a mobile station, GPS positioning device, data processing device of PDA type, pulse meter, sensor determining a user's body function, or device for showing time, said projector is a separate projector adapted to a garment worn by the user, said at least one electronic device being adapted to be connected to said projector and the projector comprising at least one light-emitting means for projecting the information to be displayed and the projector comprising additionally the optics and the electronics necessary for projecting the information to be displayed.

6. A projector as defined in claim 5, wherein said projector is at least one of the following: a projector equipped with a Resonance Cavity LED matrix, the matrix comprising at least one Resonance Cavity LED, laser projector, and micromirror projector.

7. A projector as defined in claim 5, wherein said electronics necessary for projection provided in the projector are adapted to be connected removably to the optics in the projector and to the light-emitting means.

8. A projector as defined in claim 5, wherein said electronics necessary for projection provided in the projector are adapted to be connected to the optics in the projector and to the light-emitting means by at least one of the following means: a cable, over a radio connection, and by optical means.

9. A projector as defined in claim 5, wherein said projector comprises adapter means for connecting to the projector the electronic device to be connected to the projector.

10. A projector as defined in claim 5, wherein said electronic device that can be connected to the projector is a mobile station.

11. A projector as defined in claim 5, wherein said electronic device that can be connected to the projector is a GPS positioning device.

12. A projector as defined in claim 5, wherein said electronic device that can be connected to the projector is a data processing device of PDA type.

13. A projector as defined in claim 5, wherein said electronic device is adapted to be connected to the projector by at least one of the following means: a cable, over radio connection, and by optical means.

14. A projector as defined in claim 5, wherein said projector comprises means for connecting an external control unit to the projector in order to control the projector and the image projected by the projector.

15. A projector as defined in claim 13, wherein said cable is integrated in a garment worn by the user.

16. A projector as defined in claim 5, wherein said projector comprises orientation means to project and focus information generated by the electronic device to the location indicated by the user.

17. A garment comprising projector as defined in claim 5.

18. The garment as defined in claim 17, wherein the garment comprises a rechargeable power source or solar panel adapted to be connected to the projector or at least one electronic device connected to the projector.

19. The garment as defined in claim 17, wherein the garment comprises at least one of the following module: mobile station module, GPS module, and PDA module.

20. The garment as defined in claim 17, wherein the garment comprises a fibrous wire net integrated in the garment to connect electronic device and projector electrically to each other.

21. The garment as defined in claim 17, wherein the garment is at least one of the following: a shirt, coat, pair of trousers, shoe, glove, and hat.

* * * * *

UNITED STATES PATENT AND TRADEMARK OFFICE
CERTIFICATE OF CORRECTION

PATENT NO.    : 6,830,344 B2
DATED         : December 14, 2004
INVENTOR(S)   : Akseli Reho et al.

It is certified that error appears in the above-identified patent and that said Letters Patent is hereby corrected as shown below:

Title page,
Item [75], Inventors, please delete "Akeseli" and insert -- Akseli --.

Signed and Sealed this

Twenty-third Day of August, 2005

JON W. DUDAS
*Director of the United States Patent and Trademark Office*